(12) United States Patent
Francis-Lang et al.

(10) Patent No.: US 8,632,962 B2
(45) Date of Patent: Jan. 21, 2014

(54) PLKS AS MODIFIERS OF THE BETA CATENIN PATHWAY AND METHODS OF USE

(75) Inventors: Helen Francis-Lang, San Francisco, CA (US); Christopher G. Winter, Needham, MA (US); Richard Benn Abegania Ventura, Daly City, CA (US); Lynn Margaret Bjerke, London (GB); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 1273 days.

(21) Appl. No.: 10/580,131

(22) PCT Filed: Nov. 23, 2004

(86) PCT No.: PCT/US2004/039549
§ 371 (c)(1),
(2), (4) Date: Jul. 18, 2008

(87) PCT Pub. No.: WO2005/051319
PCT Pub. Date: Jun. 9, 2005

(65) Prior Publication Data
US 2008/0274122 A1 Nov. 6, 2008

Related U.S. Application Data

(60) Provisional application No. 60/524,587, filed on Nov. 24, 2003.

(51) Int. Cl.
*C12Q 1/00* (2006.01)
*C12Q 1/68* (2006.01)
*G01N 33/53* (2006.01)

(52) U.S. Cl.
USPC .............................. 435/4; 435/6.13; 435/7.1

(58) Field of Classification Search
None
See application file for complete search history.

(56) References Cited

U.S. PATENT DOCUMENTS 5,976,893 A * 11/1999 Dennis et al. ................. 436/501
7,413,870 B2 * 8/2008 Hitoshi et al. .................. 435/15
2002/0015943 A1 2/2002 Bienz
2003/0108937 A1 6/2003 Williamson

OTHER PUBLICATIONS

Wolf et al (Oncogene, 1997, 14:543-549).*
iHOP "information hyperlinked over proteins", p. 1-3, printed Jun. 22, 2010.*
Eckerdt et al (Oncogene, 2005, 24:267-276).*
Habedanck et al (Nature Cell Biology, 2005, 7:1140-1146).*
Pellegrino et al (Hepatology, 2010, 51:857-868).*
Arai et al (Cell Cycle, 2008, 7:3556-3563).*
Spankuch-Schmitt et al (Oncogene, 2002, 21:3162-3171).*
Bahmanyar et al (J of Cell Science, 2010, 123:3125-3135).*
Hudziak et al (Antisense & Nucleic Acid Drug Development, 2000, 10:163-176).*
Hudziak, R. et al.: "Resistance of Morpholino Phosphorodiamidate Oligomers to Enzymatic Degradation," Antisense Nucleic Acid Drug Dev., vol. 6, No. 4, pp. 267-272, 1996.
Angeles et al.: "Enzyme-linked Immunosorben Assay for trkA Tyrosine Kinase Activity," Analytical Biochemistry, vol. 236, pp. 49-55, 1996.
Holtrich U. et al.: "Induction and down-regulation of PLK, a human serine/theronine kinase expressed in proliferating cells and tumors," Proceedings of the national Academy of Sciences of USA, National Academy of Science, Washington, DC, US, vol. 91, Mar. 1994, pp. 1736-1740.
Li B. et al.: "Prk, A cytokine-inducible human protein serine/threonine kinase whose expression appears to be down-regulated in lunch carcinomas," Journal of Biological Chemistry, American society of Biochemical biologists, Birmingham, US, vol. 271, No. 32, Aug. 9, 1996.
Fode C. et al.: "Sak, a murine protein-serine/threonine kinase that is related to the *Drosophila* polo kinase and involved in cell proliferation," Proceedings of the National Academy of Sciences of USA, National Academy of Science, Washington, DC, US, vol. 91, Jul. 1994, pp. 6388-6392.
Llamazares S. et al.: "Polo Encodes a Protein Kinase Homolog Required for Mitosis in *Drosophila*," Genes and Development, cold Spring Harbor, NY, US, vol. 5, No. 12A, 1991, pp. 2153-2165.
GenBank Reference No. 21361432 (NM_014264.2) entitled: "*Homo sapiens* polo-like kinase 4 (*Drosophila*) (PLK4), mRNA," dated Oct. 5, 2003.
GenBank Reference No. 7657626 (NM_014264.1) entitled: "*Homo sapiens* serine/threonine kinase 18 (STK18), mRNA," dated Nov. 2, 2000.
GenBank Reference No. 14721506 (XM_033920.1) entitled: "*Homo sapiens* serine/threonine kinase 18 (STK18), mRNA," dated May 13, 2002.
GenBank Reference No. 16215695 (AB006972.1) entitled: "*Homo sapiens* mRNA for Sak, complete cds," dated Oct. 18, 2001.
GenBank Reference No. 23243308 (BC036023.1) entitled: "*Homo sapiens* polo-like kinase 4 (*Drosophila*), mRNA (cDNA clone MGC:33045 Image:5273226), complete cds," dated Nov. 12, 2003.
GenBank Reference No. 21361433 (NP_055079.2) entitled: "polo-like kinase 4 [*Homo sapiens*]," dated Oct. 5, 2003.

* cited by examiner

*Primary Examiner* — Laura B Goddard
(74) *Attorney, Agent, or Firm* — McDonnell Boehnen Hulbert & Berghoff LLP

(57) ABSTRACT

Human PLK genes are identified as modulators of the beta catenin pathway, and thus are therapeutic targets for disorders associated with defective beta catenin function. Methods for identifying modulators of beta catenin, comprising screening for agents that modulate the activity of PLK are provided.

14 Claims, No Drawings

SEQUENCE LISTING

```
<160> NUMBER OF SEQ ID NOS: 6

<210> SEQ ID NO 1
<211> LENGTH: 3331
<212> TYPE: DNA
<213> ORGANISM: Homo sapiens

<400> SEQUENCE: 1
cagagggcac cgcccaggcc tcggaaggtg tcagggagaa ctttccgtgg tttcagcgtc      60
gtcgcctgga gcggcggttt agagagccga gcctgatggg cgccaaggcc ggctggctgc     120
ttggagcgct gcctcgaagg gactgcgtaa ggaagctaat ccggagaacc caggccagag     180
cctgaaatat ggcgacctgc atcggggaga agatcgagga ttttaaagtt ggaaatctgc     240
ttggtaaagg atcatttgct ggtgtctaca gagctgagtc cattcacagt ggtttggaag     300
ttgcaatcaa aatgatagat aagaaagcca tgtacaaagc aggaatggta cagagagtcc     360
aaaatgaggt gaaaatacat tgccaattga aacatccttc tatcttggag ctttataact     420
attttgaaga tagcaattat gtgtatctgg tattagaaat gtgccataat ggagaaatga     480
acaggtatct aaagaataga gtgaaaccct tctcagaaaa tgaagctcga cacttcatgc     540
accagatcat cacagggatg ttgtatcttc attctcatgg tatactacac cgggacctca     600
cactttctaa cctcctactg actcgtaata tgaacatcaa gattgctgat tttgggctgg     660
caactcaact gaaaatgcca catgaaaagc actatacatt atgtggaact cctaactaca     720
tttcaccaga aattgccact cgaagtgcac atggccttga atctgatgtt tggtccctgg     780
gctgtatgtt ttatacatta cttatcggga gaccaccctt cgacactgac acagtcaaga     840
acacattaaa taagtagta ttggcagatt atgaaatgcc aactttttg tcaatagagg     900 ccaaggacct tattcaccag ttacttcgta gaaatccagc agatcgttta agtctgtctt     960
cagtattgga ccatccttt atgtcccgaa attcttcaac aaaaagtaaa gatttaggaa    1020
ctgtggaaga ctcaattgat agtgggcatg ccacaatttc tactgcaatt acagcttctt    1080
ccagtaccag tataagtggt agtttatttg acaaaagaag acttttgatt ggtcagccac    1140
tcccaaataa aatgactgta tttccaaaga ataaagttc aactgattt tcttcttcag    1200 gagatggaaa cagttttat actcagtggg gaaatcaaga aaccagtaat agtggaaggg    1260
gaagagtaat tcaagatgca gaagaaaggc cacattctcg ataccttcgt agagcttatt    1320
cctctgatag atctggcact tctaatagac agtctcaagc aaaaacatat acaatggaac    1380
gatgtcactc agcagaaatg ctttcagtgt ccaaaagatc aggaggaggt gaaaatgaag    1440
```

```
agaggtactc acccacagac aacaatgcca acattttaa cttctttaaa gaaaagacat      1500
ccagtagttc tggatctttt gaaagacctg ataacaatca agcactctcc aatcatcttt      1560
gtccaggaaa aactcctttt ccatttgcag acccgacacc tcagactgaa accgtacaac      1620
agtggtttgg gaatctgcaa ataaatgctc atttaagaaa aactactgaa tatgacagca      1680
tcagcccaaa ccgggacttc cagggccatc cagatttgca gaaggacaca tcaaaaaatg      1740
cctggactga tacaaaagtc aaaagaact ctgatgcttc tgataatgca cattctgtaa       1800
aacagcaaaa taccatgaaa tatatgactg cacttcacag taaacctgag ataatccaac      1860
aagaatgtgt ttttggctca gatcctcttt ctgaacagag caagactagg ggtatggagc      1920
caccatgggg ttatcagaat cgtacattaa gaagcattac atctccgttg gttgctcaca      1980
ggttaaaacc aatcagacag aaaaccaaaa aggctgtggt gagcatactt gattcagagg      2040
aggtgtgtgt ggagcttgta aaggagtatg catctcaaga atatgtgaaa gaagttcttc      2100
agatatctag tgatggaaat acgatcacta tttattatcc aaatggtggt agaggttttc      2160
ctcttgctga tagccacccc tcacctactg acaacatcag taggtacagc tttgacaatt      2220
taccagaaaa atactggcga aaatatcaat atgcttccag gtttgtacag cttctaagat      2280
ctaaatctcc caaaatcact tattttacaa gatatgctaa atgcattttg atggagaatt      2340
ctcctggtgc tgattttgag gtttggtttt atgatgggt aaaaatacac aaaacagaag       2400
atttcattca ggtgattgaa aagacaggga agtcttacac tttaaaaagt gaaagtgaag      2460
ttaatagctt gaaagaggag ataaaaatgt atatggacca tgctaatgag ggtcatcgta      2520
tttgtttagc actggaatcc ataatttcag aagaggaaag gaaaactagg agtgctccct      2580
tttcccaat aatcatagga agaaaacctg gtagtactag ttcacctaag gcctatcac        2640
ctcctccttc tgtggattca aattacccaa cgagagatag agcatctttc aacagaatgg      2700
tcatgcatag tgatgcttct ccaacacagg caccaatcct taatccctct atggttacaa      2760
atgaaggact tggtcttaca actacagctt ctggaacaga catctcttct aatagtctaa      2820
aagattgtct tcctaaatca gcacaacttt tgaaatctgt ttttgtgaaa aatgttggtt      2880
gggctacaca gttaactagt ggagctgtgt gggttcagtt taatgatggg tcccagttgg      2940
ttgtgcaggc aggagtgtct tctatcagtt ataccacc aaatggtcaa acaactaggt         3000
atggagaaaa tgaaaaatta ccagactaca tcaaacagaa attacagtgt ctgtcttcca      3060
tccttttgat gttttctaat ccgactccta attttcattg attaaaactc ctttcagaca      3120
tataagttta ataaataact tttttgttga ctttcaagta aagtgatttt ttttaattta      3180
acataaagtc ttcagaaagc ctttctatga aagaattta acctataatg taaaccatgt       3240
atctgagata acaaagcaga atgaaacttg agtcacttac taaatatagt ggatataaaa      3300
tagaacacct gactttgctc ttagaccata a                                     3331
```

<210> SEQ ID NO 2
<211> LENGTH: 3092
<212> TYPE: DNA
<213> ORGANISM: Homo sapiens

<400> SEQUENCE: 2

```
tttcagcgtc gtcgcctgga gcggcggttt agagaaccga gcctgatggg cgccaaggcc        60
ggctggctgc ttggagcgct gcctcgaagg gcctgcgtga aggaagctaa tccggagaac       120
ccaggccaga gcctggaaat atggcgacct gcatcgggga gaagatcgag gatttttaaag      180
ttggaaatct gcttggtaaa ggatcatttg ctggtgtcta cagagctgag tccattcaca       240
```

```
ctggtttgga agttgcaatc aaaatgatag ataagaaagc catgtacaaa gcaggaatgg      300
tacagagagt caaaaatgag gtgaaaatac attgccaatt gaaacatcct tctatcttgg      360
agctttataa ctattttgaa gatagcaatt atgtgtatct ggtattagaa atgtgccata      420
atggagaaat gaacaggtat ctaaagaata gagtgaaacc cttctcagaa aatgaagctc      480
gacacttcat gcaccagatc atcacaggga tgttgtatct tcattctcat ggtatactac      540
accgggacct cacactttct aacctcctac tgactcgtaa tatgaacatc aagattgctg      600
attttgggct ggcaactcaa ctgaaaatgc cacatgaaaa gcactataca ttatgtggaa      660
ctcctaacta catttcacca gaaattgcca ctcgaagtgc acatggcctt gaatctgatg      720
tttggtccct gggctgtatg ttttatacat tacttatcgg gagaccaccc ttcgacactg      780
acacagtcaa gaacacatta aataaagtag tattggcaga ttatgaaatg ccaacttttt      840
tgtcaataga ggccaaggac cttattcacc agttacttcg tagaaatcca gcagatcgtt      900
taagtctgtc ttcagtattg gaccatcctt ttatgtcccg aaattcttca acaaaaagta      960
aagatttagg aactgtggaa gactcaattg atagtgggca tgccacaatt tctactgcaa     1020
ttacagcttc ttccagtacc agtataagtg gtagtttatt tgacaaaaga agactttga     1080 ttggtcagcc actcccaaat aaaatgactg tatttccaaa gaataaagt tcaactgatt     1140 tttcttcttc aggagatgga aacagttttt atactcagtg gggaaatcaa gaaaccagta     1200
atagtggaag gggaagagta attcaagatg cagaagaaag gccacattct cgataccttc     1260
gtagagctta ttcctctgat agatctggca cttctaatag tcagtctcaa gcaaaaacat     1320
atacaatgga acgatgtcac tcagcagaaa tgctttcagt gtccaaaaga tcaggaggag     1380
gtgaaaatga agagaggtac tcacccacag acaacaatgc caacattttt aacttcttta     1440
aagaaaagac atccagtagt tctggatctt ttgaaagacc tgataacaat caagcactct     1500
ccaatcatct ttgtccagga aaaactcctt ttccatttgc agacccgaca cctcagactg     1560
aaaccgtaca acagtggttt gggaatctgc aaataaatgc tcatttaaga aaaactactg     1620
aatatgacag catcagccca aaccgggact tccagggcca tccagatttg cagaaggaca     1680
catcaaaaaa tgcctggact gatacaaaag tcaaaaagaa ctctgatgct tctgataatg     1740
cacattctgt aaaacagcaa aataccatga aatatatgac tgcacttcac agtaaacctg     1800
agataatcca acaagaatgt gttttttggct cagatcctct ttctgaacag agcaagacta     1860
ggggtatgga gccaccatgg ggttatcaga atcgtacatt aagaagcatt acatctccgt     1920
tggttgctca caggttaaaa ccaatcagac agaaaaccaa aaaggctgtg gtgagcatac     1980
ttgattcaga ggaggtgtgt gtggagcttg taaaggagta tgcatctcaa gaatatgtga     2040
aagaagttct tcagatatct agtgatggaa atacgatcac tatttattat ccaaatggtg     2100
gtagaggttt tcctcttgct gatagaccac cctcacctac tgacaacatc agtaggtaca     2160
gctttgacaa tttaccagaa aaatactggc gaaaatatca atatgcttcc aggtttgtac     2220
agcttgtaag atctaaatct cccaaaatca cttattttac aagatatgct aaatgcattt     2280
tgatggagaa ttctcctggt gctgattttg aggtttggtt ttatgatggg gtaaaaatac     2340
acaaaacaga agatttcatt caggtgattg aaaagacagg gaagtcttac actttaaaaa     2400
gtgaaagtga agttaatagc ttgaaagagg agataaaaat gttatggac catgctaatg     2460 agggtcatcg tatttgttta gcactggaat ccataatttc agaagaggaa aggaaaacta     2520
ggagtgctcc cttttttccca ataatcatag gaagaaaacc aggtagtact agttcaccta     2580
aggccttatc acctcctcct tctgtggatt caaattaccc aacgagagat agagcatctt     2640
```

| | |
|---|---|
| tcaacagaat ggtcatgcat agtgctgctt ctccaacaca ggcaccaatc cttaatccct | 2700 |
| ctatggttac aaatgaagga cttggtctta caactacagc ttctggaaca gacatctctt | 2760 |
| ctaatagtct aaaagattgt cttcctaaat cagcacaact tttgaaatct gtttttgtga | 2820 |
| aaaatgttgg ttgggctaca cagttaacta gtggagctgt gtgggttcag tttaatgatg | 2880 |
| ggtcccagtt ggttgtgcag gcaggagtgt cttctatcag ttatacctca ccaaatggtc | 2940 |
| aaacaactag gtatggagaa aatgaaaaat taccagacta catcaaacag aaattacagt | 3000 |
| gtctgtcttc catcctttg atgttttcta atccgactcc taattttcat tgattaaaac | 3060 |
| tcctttcaga catataagtt taataaataa ct | 3092 |

<210> SEQ ID NO 3
<211> LENGTH: 3092
<212> TYPE: DNA
<213> ORGANISM: Homo sapiens

<400> SEQUENCE: 3

| | |
|---|---|
| tttcagcgtc gtcgcctgga gcggcggttt agagagccga gcctgatggg cgccaaggcc | 60 |
| ggctggctgc ttggagcgct gcctcgaagg gactgcgtga aggaagctaa tccggagaac | 120 |
| ccaggccaga gcctggaaat atggcgacct gcatcgggga aagatcgag gattttaaag | 180 |
| ttggaaatct gcttggtaaa ggatcatttg ctggtgtcta cagagctgag tccattcaca | 240 |
| ctggtttgga agttgcaatc aaaatgatag ataagaaagc catgtacaaa gcaggaatgg | 300 |
| tacagagagt ccaaaatgag gtgaaaatac attgccaatt gaaacatcct tctatcttgg | 360 |
| agctttataa ctattttgaa gatagcaatt atgtgtatct ggtattagaa atgtgccata | 420 |
| atggagaaat gaacaggtat ctaaagaata gagtgaaacc cttctcagaa atgaagctc | 480 |
| gacacttcat gcaccagatc atcacaggga tgttgtatct tcattctcat ggtatactac | 540 |
| accgggacct cacactttct aacctcctac tgactcgtaa tatgaacatc aagattgctg | 600 |
| attttgggct ggcaactcaa ctgaaaatgc cacatgaaaa gcactataca ttatgtggaa | 660 |
| ctcctaacta catttcacca gaaattgcca ctcgaagtgc acatggcctt gaatctgatg | 720 |
| tttggtccct gggctgtatg ttttatacat tacttatcgg gagaccaccc ttcgacactg | 780 |
| acacagtcaa gaacacatta aataaagtag tattggcaga ttatgaaatg ccatcttttt | 840 |
| tgtcaataga ggccaaggac cttattcacc agttacttcg tagaaatcca gcagatcgtt | 900 |
| taagtctgtc ttcagtattg gaccatcctt ttatgtcccg aaattcttca acaaaaagta | 960 |
| aagatttagg aactgtggaa gactcaattg atagtgggca tgccacaatt tctactgcaa | 1020 |
| ttacagcttc ttccagtacc agtataagtg gtagtttatt tgacaaaaga agacttttga | 1080 |
| ttggtcagcc actcccaaat aaaatgactg tatttccaaa gaataaaagt tcaactgatt | 1140 |
| tttcttcttc aggagatgga aacagttttt atactcagtg gggaaatcaa gaaccagta | 1200 |
| atagtggaag gggaagagta attcaagatg cagaagaaag gccacattct cgatacttc | 1260 |
| gtagagctta ttcctctgat agatctggca cttctaatag tcagtctcaa gcaaaaacat | 1320 |
| atacaatgga acgatgtcac tcagcagaaa tgctttcagt gtccaaaaga tcaggaggag | 1380 |
| gtgaaaatga agagaggtac tcacccacag acaacaatgc caacatttt aacttcttta | 1440 |
| aagaaaagac atccagtagt tctggatctt ttgaagacc tgataacaat caagcactct | 1500 |
| ccaatcatct ttgtccagga aaaactcctt ttccatttgc agacccgaca cctcagactg | 1560 |
| aaaccgtaca acagtggttt gggaatctgc aaataaatgc tcatttaaga aaaactactg | 1620 |
| aatatgacag catcagccca aaccgggact tccagggcca tccagatttg cagaaggaca | 1680 |

```
catcaaaaaa tgcctggact gatacaaaag tcaaaagaa ctctgatgct tctgataatg      1740
cacattctgt aaacagcaa ataccatga aatatatgac tgcacttcac agtaaacctg       1800
agataatcca acaagaatgt gttttttggct cagatcctct ttctgaacag agcaagacta    1860
ggggtatgga gccaccatgg ggttatcaga atcgtacatt aagaagcatt acatctccgt    1920
tggttgctca caggttaaaa ccaatcagac agaaaaccaa aaaggctgtg gtgagcatac    1980
ttgattcaga ggaggtgtgt gtggagcttg taaaggagta tgcatctcaa gaatatgtga    2040
aagaagttct tcagatatct agtgatgaa atacgatcac tatttattat ccaaatggtg     2100
gtagaggttt tcctcttgct gatagaccac cctcacctac tgacaacatc agtaggtaca    2160
gctttgacaa tttaccagaa aaatactggc gaaaatatca atatgcttcc aggtttgtac    2220
agcttgtaag atctaaatct cccaaaatca cttattttac aagatatgct aaatgcattt    2280
tgatggagaa ttctcctggt gctgattttg aggtttggtt ttatgatggg gtaaaaatac    2340
acaaaacaga agatttcatt caggtgattg aaaagacagg gaagtcttac actttaaaaa    2400
gtgaaagtga agttaatagc ttgaaagagg agataaaaat gtatatggac catgctaatg    2460
agggtcatcg tatttgttta gcactggaat ccataatttc agaagaggaa aggaaaacta    2520
ggagtgctcc cttttttccca ataatcatag gaagaaaacc tggtagtact agttcaccta   2580
aggccttatc acctcctcct tctgtggatt caaattaccc aacgagagag agagcatctt    2640
tcaacagaat ggtcatgcat agtgctgctt ctccaacaca ggcaccaatc cttaatccct    2700
ctatggttac aaatgaagga cttggtctta caactacagc ttctggaaca gacatctctt    2760
ctaatagtct aaaagattgt cttcctaaat cagcacaact tttgaaatct gttttttgtga   2820 aaaatgttgg ttgggctaca cagttaacta gtggagctgt gtgggttcag tttaatgatg    2880
ggtcccagtt ggttgtgcag gcaggagtgt cttctatcag ttatacctca ccaaatggtc    2940
aaacaactag gtatggagaa aatgaaaaat taccagacta catcaaacag aaattacagt    3000
gtctgtcttc catccttttg atgttttcta atccgactcc taattttcat tgattaaaac    3060
tcctttcaga catataagtt taataaataa ct                                  3092
```

<210> SEQ ID NO 4
<211> LENGTH: 3331
<212> TYPE: DNA
<213> ORGANISM: Homo sapiens

<400> SEQUENCE: 4

```
cagagggcac cgcccaggcc tcggaaggtg tcagggagaa cttttccgtgg tttcagcgtc     60 gtcgcctgga gcggcggttt agagagccga gcctgatggg cgccaaggcc ggctggctgc    120
ttggagcgct gcctcgaagg gactgcgtaa ggaagctaat ccggagaacc caggccagag    180
cctgaaatat ggcgacctgc atcgggaga agatcgagga ttttaaagtt ggaaatctgc    240
ttggtaaagg atcatttgct ggtgtctaca gagctgagtc cattcacagt ggtttggaag    300
ttgcaatcaa aatgatagat aagaaagcca tgtacaaagc aggaatggta cagagagtcc    360
aaaatgaggt gaaaatacat tgccaattga acatccttc tatcttggag ctttataact    420
attttgaaga tagcaattat gtgtatctgg tattagaaat gtgccataat ggagaaatga    480
acaggtatct aaagaataga gtgaaaccct ctcagaaaaa tgaagctcga cacttcatgc    540
accagatcat cacagggatg ttgtatcttc attctcatgg tatactacac cgggacctca    600 cacttttctaa cctcctactg actcgtaata tgaacatcaa gattgctgat tttgggctgg    660
caactcaact gaaaatgcca catgaaaagc actatacatt atgtggaact cctaactaca    720
```

```
tttcaccaga aattgccact cgaagtgcac atggccttga atctgatgtt tggtccctgg      780
gctgtatgtt ttatacatta cttatcggga gaccacccct cgacactgac acagtcaaga      840
acacattaaa taaagtagta ttggcagatt atgaaatgcc aacttttttg tcaatagagg      900
ccaaggacct tattcaccag ttacttcgta gaaatccagc agatcgttta agtctgtctt      960
cagtattgga ccatcctttt atgtcccgaa attcttcaac aaaaagtaaa gatttaggaa     1020
ctgtggaaga ctcaattgat agtgggcatg ccacaatttc tactgcaatt acagcttctt     1080
ccagtaccag tataagtggt agtttatttg acaaaagaag acttttgatt ggtcagccac     1140
tcccaaataa aatgactgta tttccaaaga ataaaagttc aactgatttt tcttcttcag     1200
gagatggaaa cagtttttat actcagtggg gaaatcaaga aaccagtaat agtggaaggg     1260
gaagagtaat tcaagatgca gaagaaaggc cacattctcg ataccttcgt agagcttatt     1320
cctctgatag atctggcact tctaatagac agtctcaagc aaaaacatat acaatggaac     1380
gatgtcactc agcagaaatg ctttcagtgt ccaaaagatc aggaggaggt gaaaatgaag     1440
agaggtactc acccacagac aacaatgcca acatttttaa cttctttaaa gaaaagacat     1500
ccagtagttc tggatctttt gaaagacctg ataacaatca agcactctcc aatcatcttt     1560
gtccaggaaa aactcctttt ccatttgcag acccgacacc tcagactgaa accgtacaac     1620
agtggtttgg gaatctgcaa ataaatgctc atttaagaaa aactactgaa tatgacagca     1680
tcagcccaaa ccgggacttc cagggccatc agatttgca gaaggacaca tcaaaaaatg     1740
cctggactga tacaaaagtc aaaaagaact ctgatgcttc tgataatgca cattctgtaa     1800
aacagcaaaa taccatgaaa tatatgactg cacttcacag taaacctgag ataatccaac     1860
aagaatgtgt ttttggctca gatcctcttt ctgaacagag caagactagg ggtatggagc     1920
caccatgggg ttatcagaat cgtacattaa gaagcattac atctccgttg gttgctcaca     1980
ggttaaaacc aatcagacag aaaaccaaaa aggctgtggt gagcatactt gattcagagg     2040
aggtgtgtgt ggagcttgta aaggagtatg catctcaaga atatgtgaaa gaagttcttc     2100
agatatctag tgatggaaat acgatcacta tttattatcc aaatggtggt agaggttttc     2160
ctcttgctga tagcaccccc tcacctactg acaacatcag taggtacagc tttgacaatt     2220
taccagaaaa atactggcga aaatatcaat atgcttccag gtttgtacag cttctaagat     2280
ctaaatctcc caaaatcact tattttacaa gatatgctaa atgcattttg atggagaatt     2340
ctcctggtgc tgattttgag gtttggtttt atgatgggt aaaaatacac aaaacagaag     2400
atttcattca ggtgattgaa aagacaggga agtcttacac tttaaaaagt gaaagtgaag     2460
ttaatagctt gaaagaggag ataaaaatgt atatggacca tgctaatgag ggtcatcgta     2520
tttgtttagc actggaatcc ataatttcag aagaggaaag gaaaactagg agtgctccct     2580
ttttcccaat aatcatagga agaaaacctg gtagtactag ttcacctaag gccttatcac     2640
ctcctccttc tgtggattca aattacccaa cgagagatag agcatctttc aacagaatgg     2700
tcatgcatag tgatgcttct ccaacacagg caccaatcct taatccctct atggttacaa     2760
atgaaggact tggtcttaca actacagctt ctggaacaga catctcttct aatagtctaa     2820
aagattgtct tcctaaatca gcacaacttt tgaaatctgt ttttgtgaaa atgttggtt      2880 gggctacaca gttaactagt ggagctgtgt gggttcagtt taatgatggg tcccagttgg     2940
ttgtgcaggc aggagtgtct tctatcagtt atacctcacc aaatggtcaa acaactaggt     3000
atggagaaaa tgaaaaatta ccagactaca tcaaacagaa attacagtgt ctgtcttcca     3060
tccttttgat gttttctaat ccgactccta attttcattg attaaaactc ctttcagaca     3120
```

-continued

| | |
|---|---:|
| tataagttta ataaataact tttttgttga ctttcaagta aagtgatttt ttttaattta | 3180 |
| acataaagtc ttcagaaagc ctttctatga aagaatttta acctataatg taaaccatgt | 3240 |
| atctgagata acaaagcaga atgaaacttg agtcacttac taaatatagt ggatataaaa | 3300 |
| tagaacacct gactttgctc ttagaccata a | 3331 |

<210> SEQ ID NO 5
<211> LENGTH: 3225
<212> TYPE: DNA
<213> ORGANISM: Homo sapiens

<400> SEQUENCE: 5

| | |
|---|---:|
| accaccagcc tagctcggac ggcaagcggc gggagatttt caaaatggga gcccagaggc | 60 |
| accgcccagg cctcggaagg tgtcagggag aactttccgt ggtttcagcg tcgtcgcctg | 120 |
| gagcggcggt ttagagagcc gagcctgatg ggcgccaagg ccggctggct gcttggagcg | 180 |
| ctgcctcgaa gggactgcgt gaaggaagct aatccggaga acccaggcca gagcctggaa | 240 |
| atatggcgac ctgcatcggg gagaagatcg aggattttaa agttggaaat ctgcttggta | 300 |
| aaggatcatt tgctggtgtc tacagagctg agtccattca cactggtttg gaagttgcaa | 360 |
| tcaaaatgat agataagaaa gccatgtaca agcaggaat ggtacagaga gtccaaaatg | 420 |
| aggtgaaaat acattgccaa ttgaaacatc cttctatctt ggagctttat aactattttg | 480 |
| aagatagcaa ttatgtgtat ctggtattag aaatgtgcca taatggagaa atgaacaggt | 540 |
| atctaaagaa tagagtgaaa cccttctcag aaaatgaagc tcgacacttc atgcaccaga | 600 |
| tcatcacagg gatgttgtat cttcattctc atggtatact acaccgggac ctcacacttt | 660 |
| ctaacctcct actgactcgt aatatgaaca tcaagattgc tgattttggg ctggcaactc | 720 |
| aactgaaaat gccacatgaa aagcactata cattatgtgg aactcctaac tacatttcac | 780 |
| cagaaattgc cactcgaagt gcacatggcc ttgaatctga tgtttggtcc ctgggctgta | 840 |
| tgttttatac attacttatc gggagaccac ccttcgacac tgacacagtc aagaacacat | 900 |
| taaataaagt agtattggca gattatgaaa tgccatcttt tttgtcaata gaggccaagg | 960 |
| accttattca ccagttactt cgtagaaatc cagcagatcg tttaagtctg tcttcagtat | 1020 |
| tggaccatcc ttttatgtcc cgaaattctt caacaaaaag taaagattta ggaactgtgg | 1080 |
| aagactcaat tgatagtggg catgccacaa tttctactgc aattacagct tcttccagta | 1140 |
| ccagtataag tggtagttta tttgacaaaa gaagactttt gattggtcag ccactcccaa | 1200 |
| ataaaatgac tgtatttcca aagaataaaa gttcaactga ttttcttct tcaggagatg | 1260 |
| gaaacagttt ttatactcag tggggaaatc aagaaaccag taatagtgga aggggaagag | 1320 |
| taattcaaga tgcagaagaa aggccacatt ctcgatacct tcgtagagct tattcctctg | 1380 |
| atagatctgg cacttctaat agtcagtctc aagcaaaaac atatacaatg aacgatgtc | 1440 |
| actcagcaga aatgctttca gtgtccaaaa gatcaggagg aggtgaaaat gaagagaggt | 1500 |
| actcacccac agacaacaat gccaacattt ttaacttctt taagaaaag acatccagta | 1560 |
| gttctggatc ttttgaaaga cctgataaca atcaagcact ctccaatcat ctttgtccag | 1620 |
| gaaaaactcc ttttccattt gcagacccga cacctcagac tgaaaccgta caacagtggt | 1680 |
| ttgggaatct gcaaataaat gctcatttaa gaaaaactac tgaatatgac agcatcagcc | 1740 |
| caaaccggga cttccagggc catccagatt tgcagaagga cacatcaaaa aatgcctgga | 1800 |
| ctgatacaaa agtcaaaaag aactctgatg cttctgataa tgcacattct gtaaaacagc | 1860 |
| aaaataccat gaaatatatg actgcacttc acagtaaacc tgagataatc caacaagaat | 1920 |

```
gtgtttttgg ctcagatcct ctttctgaac agagcaagac tagggg tatg gagccaccat    1980 ggggttatca gaatcgtaca ttaagaagca ttacatctcc gttggttgct cacaggttaa    2040
aaccaatcag acagaaaacc aaaaaggctg tggtgagcat acttgattca gaggaggtgt    2100
gtgtggagct tgtaaaggag tatgcatctc aagaatatgt gaaagaagtt cttcagatat    2160
ctagtgatgg aaatacgatc actatttatt atccaaatgg tggtagaggt tttcctcttg    2220
ctgatagacc accctcacct actgacaaca tcagtaggta cagctttgac aatttaccag    2280
aaaaatactg gcgaaaatat caatatgctt ccaggtttgt acagcttgta agatctaaat    2340
ctcccaaaat cacttatttt acaagatatg ctaaatgcat tttgatggag aattctcctg    2400
gtgctgattt tgaggtttgg ttttatgatg gggtaaaaat acacaaaaca gaagatttca    2460
ttcaggtgat tgaaaagaca gggaagtctt cacactttaaa aagtgaaagt gaagttaata    2520
gcttgaaaga ggagataaaa atgtatatgg accatgctaa tgagggtcat cgtatttgtt    2580
tagcactgga atccataatt tcagaagagg aaggaaaac taggagtgct cccttttttcc    2640 caataatcat aggaagaaaa cctggtagta ctagttcacc taaggcctta tcacctcctc    2700
cttctgtgga ttcaaattac ccaacgagag agagagcatc tttcaacaga atggtcatgc    2760
atagtgctgc ttctccaaca caggcaccaa tccttaatcc ctctatggtt acaaatgaag    2820
gacttggtct tacaactaca gcttctggaa cagacatctc ttctaatagt ctaaaagatt    2880
gtcttcctaa atcagcacaa cttttgaaat ctgttttttgt gaaaaatgtt ggttgggcta    2940
cacagttaac tagtggagct gtgtgggttc agtttaatga tgggtcccag ttggttgtgc    3000
aggcaggagt gtcttctatc agttataccct caccaaatgg tcaaacaact aggtatggag    3060
aaaatgaaaa attaccagac tacatcaaac agaaattaca gtgtctgtct tccatccttt    3120
tgatgttttc taatccgact cctaattttc attgattaaa actccttttca gacatataag    3180 tttaataaat aacttttttg ttgactttca aaaaaaaaaaa aaaaa    3225

<210> SEQ ID NO 6
<211> LENGTH: 970
<212> TYPE: PRT
<213> ORGANISM: Homo sapiens

<400> SEQUENCE: 6

Met Ala Thr Cys Ile Gly Glu Lys Ile Glu Asp Phe Lys Val Gly Asn
1               5                   10                  15

Leu Leu Gly Lys Gly Ser Phe Ala Gly Val Tyr Arg Ala Glu Ser Ile
            20                  25                  30

His Ser Gly Leu Glu Val Ala Ile Lys Met Ile Asp Lys Lys Ala Met
        35                  40                  45

Tyr Lys Ala Gly Met Val Gln Arg Val Gln Asn Glu Val Lys Ile His
    50                  55                  60

Cys Gln Leu Lys His Pro Ser Ile Leu Glu Leu Tyr Asn Tyr Phe Glu
65                  70                  75                  80

Asp Ser Asn Tyr Val Tyr Leu Val Leu Glu Met Cys His Asn Gly Glu
                85                  90                  95

Met Asn Arg Tyr Leu Lys Asn Arg Val Lys Pro Phe Ser Glu Asn Glu
            100                 105                 110

Ala Arg His Phe Met His Gln Ile Ile Thr Gly Met Leu Tyr Leu His
        115                 120                 125

Ser His Gly Ile Leu His Arg Asp Leu Thr Leu Ser Asn Leu Leu Leu
    130                 135                 140
```

-continued

```
Thr Arg Asn Met Asn Ile Lys Ile Ala Asp Phe Gly Leu Ala Thr Gln
145                 150                 155                 160

Leu Lys Met Pro His Glu Lys His Tyr Thr Leu Cys Gly Thr Pro Asn
                165                 170                 175

Tyr Ile Ser Pro Glu Ile Ala Thr Arg Ser Ala His Gly Leu Glu Ser
            180                 185                 190

Asp Val Trp Ser Leu Gly Cys Met Phe Tyr Thr Leu Leu Ile Gly Arg
        195                 200                 205

Pro Pro Phe Asp Thr Asp Thr Val Lys Asn Thr Leu Asn Lys Val Val
210                 215                 220

Leu Ala Asp Tyr Glu Met Pro Thr Phe Leu Ser Ile Glu Ala Lys Asp
225                 230                 235                 240

Leu Ile His Gln Leu Leu Arg Arg Asn Pro Ala Asp Arg Leu Ser Leu
                245                 250                 255

Ser Ser Val Leu Asp His Pro Phe Met Ser Arg Asn Ser Ser Thr Lys
            260                 265                 270

Ser Lys Asp Leu Gly Thr Val Glu Asp Ser Ile Asp Ser Gly His Ala
        275                 280                 285

Thr Ile Ser Thr Ala Ile Thr Ala Ser Ser Thr Ser Ile Ser Gly
290                 295                 300

Ser Leu Phe Asp Lys Arg Arg Leu Leu Ile Gly Gln Pro Leu Pro Asn
305                 310                 315                 320

Lys Met Thr Val Phe Pro Lys Asn Lys Ser Thr Asp Phe Ser Ser
                325                 330                 335

Ser Gly Asp Gly Asn Ser Phe Tyr Thr Gln Trp Gly Asn Gln Glu Thr
            340                 345                 350

Ser Asn Ser Gly Arg Gly Arg Val Ile Gln Asp Ala Glu Glu Arg Pro
        355                 360                 365

His Ser Arg Tyr Leu Arg Arg Ala Tyr Ser Ser Asp Arg Ser Gly Thr
370                 375                 380

Ser Asn Arg Gln Ser Gln Ala Lys Thr Tyr Thr Met Glu Arg Cys His
385                 390                 395                 400

Ser Ala Glu Met Leu Ser Val Ser Lys Arg Ser Gly Gly Gly Glu Asn
                405                 410                 415

Glu Glu Arg Tyr Ser Pro Thr Asp Asn Asn Ala Asn Ile Phe Asn Phe
            420                 425                 430

Phe Lys Glu Lys Thr Ser Ser Ser Gly Ser Phe Glu Arg Pro Asp
        435                 440                 445

Asn Asn Gln Ala Leu Ser Asn His Leu Cys Pro Gly Lys Thr Pro Phe
450                 455                 460

Pro Phe Ala Asp Pro Thr Pro Gln Thr Glu Thr Val Gln Gln Trp Phe
465                 470                 475                 480

Gly Asn Leu Gln Ile Asn Ala His Leu Arg Lys Thr Thr Glu Tyr Asp
                485                 490                 495

Ser Ile Ser Pro Asn Arg Asp Phe Gln Gly His Pro Asp Leu Gln Lys
            500                 505                 510

Asp Thr Ser Lys Asn Ala Trp Thr Asp Thr Lys Val Lys Lys Asn Ser
        515                 520                 525

Asp Ala Ser Asp Asn Ala His Ser Val Lys Gln Gln Asn Thr Met Lys
530                 535                 540

Tyr Met Thr Ala Leu His Ser Lys Pro Glu Ile Ile Gln Gln Glu Cys
545                 550                 555                 560

Val Phe Gly Ser Asp Pro Leu Ser Glu Gln Ser Lys Thr Arg Gly Met
                565                 570                 575
```

-continued

```
Glu Pro Pro Trp Gly Tyr Gln Asn Arg Thr Leu Arg Ser Ile Thr Ser
            580                 585                 590
Pro Leu Val Ala His Arg Leu Lys Pro Ile Arg Gln Lys Thr Lys Lys
            595                 600                 605
Ala Val Val Ser Ile Leu Asp Ser Glu Glu Val Cys Val Glu Leu Val
610                 615                 620
Lys Glu Tyr Ala Ser Gln Glu Tyr Val Lys Glu Val Leu Gln Ile Ser
625                 630                 635                 640
Ser Asp Gly Asn Thr Ile Thr Ile Tyr Tyr Pro Asn Gly Gly Arg Gly
                645                 650                 655
Phe Pro Leu Ala Asp Arg Pro Pro Ser Pro Thr Asp Asn Ile Ser Arg
                660                 665                 670
Tyr Ser Phe Asp Asn Leu Pro Glu Lys Tyr Trp Arg Lys Tyr Gln Tyr
            675                 680                 685
Ala Ser Arg Phe Val Gln Leu Leu Arg Ser Lys Ser Pro Lys Ile Thr
            690                 695                 700
Tyr Phe Thr Arg Tyr Ala Lys Cys Ile Leu Met Glu Asn Ser Pro Gly
705                 710                 715                 720
Ala Asp Phe Glu Val Trp Phe Tyr Asp Gly Val Lys Ile His Lys Thr
                725                 730                 735
Glu Asp Phe Ile Gln Val Ile Glu Lys Thr Gly Lys Ser Tyr Thr Leu
                740                 745                 750
Lys Ser Glu Ser Glu Val Asn Ser Leu Lys Glu Ile Lys Met Tyr
            755                 760                 765
Met Asp His Ala Asn Glu Gly His Arg Ile Cys Leu Ala Leu Glu Ser
770                 775                 780
Ile Ile Ser Glu Glu Arg Lys Thr Arg Ser Ala Pro Phe Phe Pro
785                 790                 795                 800
Ile Ile Ile Gly Arg Lys Pro Gly Ser Thr Ser Ser Pro Lys Ala Leu
                805                 810                 815
Ser Pro Pro Pro Ser Val Asp Ser Asn Tyr Pro Thr Arg Asp Arg Ala
                820                 825                 830
Ser Phe Asn Arg Met Val Met His Ser Asp Ala Ser Pro Thr Gln Ala
            835                 840                 845
Pro Ile Leu Asn Pro Ser Met Val Thr Asn Glu Gly Leu Gly Leu Thr
            850                 855                 860
Thr Thr Ala Ser Gly Thr Asp Ile Ser Ser Asn Ser Leu Lys Asp Cys
865                 870                 875                 880
Leu Pro Lys Ser Ala Gln Leu Leu Lys Ser Val Phe Val Lys Asn Val
                885                 890                 895
Gly Trp Ala Thr Gln Leu Thr Ser Gly Ala Val Trp Val Gln Phe Asn
                900                 905                 910
Asp Gly Ser Gln Leu Val Val Gln Ala Gly Val Ser Ser Ile Ser Tyr
            915                 920                 925
Thr Ser Pro Asn Gly Gln Thr Thr Arg Tyr Gly Glu Asn Glu Lys Leu
            930                 935                 940
Pro Asp Tyr Ile Lys Gln Lys Leu Gln Cys Leu Ser Ser Ile Leu Leu
945                 950                 955                 960
Met Phe Ser Asn Pro Thr Pro Asn Phe His
                965                 970
```

PLKS AS MODIFIERS OF THE BETA CATENIN PATHWAY AND METHODS OF USE

REFERENCE TO RELATED APPLICATIONS

This application claims priority to U.S. provisional patent application 60/524,587 filed Nov. 24, 2003. The contents of the prior application are hereby incorporated in their entirety.

BACKGROUND OF THE INVENTION

The *Drosophila Melanogaster* Armadillo/beta-catenin protein is implicated in multiple cellular functions. The protein functions in cell signaling via the Wingless (Wg)/Wnt signaling pathway. It also functions as a cell adhesion protein at the cell membrane in a complex with E-cadherin and alpha-catenin (Cox et al. (1996) J. Cell Biol. 134: 133-148; Godt and Tepass (1998) Nature 395: 387-391; White et al. (1998) J Cell biol. 140:183-195). These two roles of beta-catenin can be separated from each other (Orsulic and Peifer (1996) J. Cell Biol. 134: 1283-1300; Sanson et al. (1996) Nature 383: 627-630).

In Wingless cell signaling, beta-catenin levels are tightly regulated by a complex containing APC, Axin, and GSK3 beta/SGG/ZW3 (Peifer et al. (1994) Development 120: 369-380).

The Wingless/beta-catenin signaling pathway is frequently mutated in human cancers, particularly those of the colon. Mutations in the tumor suppressor gene APC, as well as point mutations in beta-catenin itself lead to the stabilization of the beta-catenin protein and inappropriate activation of this pathway.

Chromosomal segregation during mitosis and meiosis is regulated by kinases and phosphatases. Polo Like Kinase 4 (PLK4; Serine threonine kinase 18; STK18; Snk/Plk-akin kinase; SAK) is a serine threonine kinase that shares significant homology with other STKs, particularly to those related to *Drosophila* 'polo' and mouse SAK, all of which have an N-terminal kinase domain. The mouse SAK is involved in mitosis and cell division.

The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechier B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as beta catenin, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the beta catenin pathway in and *Drosophila*, and identified their human orthologs, hereinafter referred to as Polo Like Kinase (PLK). The invention provides methods for utilizing these beta catenin modifier genes and polypeptides to identify PLK-modulating agents that are candidate therapeutic agents that can be used in the treatment of disorders associated with defective or impaired beta catenin function and/or PLK function. Preferred PLK-modulating agents specifically bind to PLK polypeptides and restore beta catenin function. Other preferred PLK-modulating agents are nucleic acid modulators such as antisense oligomers and RNAi that repress PLK gene expression or product activity by, for example, binding to and inhibiting the respective nucleic acid (i.e. DNA or mRNA).

PLK modulating agents may be evaluated by any convenient in vitro or in vivo assay for molecular interaction with a PLK polypeptide or nucleic acid. In one embodiment, candidate PLK modulating agents are tested with an assay system comprising a PLK polypeptide or nucleic acid. Agents that produce a change in the activity of the assay system relative to controls are identified as candidate beta catenin modulating agents. The assay system may be cell-based or cell-free. PLK-modulating agents include PLK related proteins (e.g. dominant negative mutants, and biotherapeutics); PLK-specific antibodies; PLK-specific antisense oligomers and other nucleic acid modulators; and chemical agents that specifically bind to or interact with PLK or compete with PLK binding partner (e.g. by binding to a PLK binding partner). In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate beta catenin pathway modulating agents are further tested using a second assay system that detects changes in the beta catenin pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the beta catenin pathway, such as an angiogenic, apoptotic, or cell proliferation disorder (e.g. cancer).

The invention further provides methods for modulating the PLK function and/or the beta catenin pathway in a mammalian cell by contacting the mammalian cell with an agent that specifically binds a PLK polypeptide or nucleic acid. The agent may be a small molecule modulator, a nucleic acid modulator, or an antibody and may be administered to a mammalian animal predetermined to have a pathology associated with the beta catenin pathway.

DETAILED DESCRIPTION OF THE INVENTION

In a screen to identify enhancers and suppressors of the Wg signaling pathway, we generated activated beta-catenin models in *Drosophila* based on human tumor data (Polakis (2000) Genes and Development 14: 1837-1851). The POLO gene was identified as a modifier of the beta catenin pathway. Accordingly, vertebrate orthologs of these modifiers, and preferably the human orthologs, PLK genes (i.e., nucleic acids and polypeptides) are attractive drug targets for the treatment of pathologies associated with a defective beta catenin signaling pathway, such as cancer.

In vitro and in vivo methods of assessing PLK function are provided herein. Modulation of the PLK or their respective binding partners is useful for understanding the association of the beta catenin pathway and its members in normal and disease conditions and for developing diagnostics and therapeutic modalities for beta catenin related pathologies. PLK-modulating agents that act by inhibiting or enhancing PLK expression, directly or indirectly, for example, by affecting a PLK function such as enzymatic (e.g., catalytic) or binding activity, can be identified using methods provided herein. PLK modulating agents are useful in diagnosis, therapy and pharmaceutical development.

Nucleic Acids and Polypeptides of the Invention

Sequences related to PLK nucleic acids and polypeptides that can be used in the invention are disclosed in Genbank (referenced by Genbank identifier (GI) number) as GI#s 21361432 (SEQ ID NO: 1), 7657626 (SEQ ID NO:2), 14721506 (SEQ ID NO:3), 16215695 (SEQ ID NO:4), and 23243308 (SEQ ID NO:5) for nucleic acid, and GI#21361432 (SEQ ID NO:6) for polypeptide sequences.

The term "PLK polypeptide" refers to a full-length PLK protein or a functionally active fragment or derivative thereof. A "functionally active" PLK fragment or derivative exhibits one or more functional activities associated with a full-length, wild-type PLK protein, such as antigenic or immunogenic activity, enzymatic activity, ability to bind natural cellular substrates, etc. The functional activity of PLK proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active PLK polypeptide is a PLK derivative capable of rescuing defective endogenous PLK activity, such as in cell based or animal assays; the rescuing derivative may be from the same or a different species. For purposes herein, functionally active fragments also include those fragments that comprise one or more structural domains of a PLK, such as a kinase domain or a binding domain. Protein domains can be identified using the PFAM program (Bateman A., et al., Nucleic Acids Res, 1999, 27:260-2). For example, the Protein kinase domain (PFAM 00069) of PLK from GI#21361433 (SEQ ID NO:6) is located at approximately amino acid residues 12-265. Methods for obtaining PLK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a PLK. In further preferred embodiments, the fragment comprises the entire functionally active domain.

The term "PLK nucleic acid" refers to a DNA or RNA molecule that encodes a PLK polypeptide. Preferably, the PLK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human PLK. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a PLK. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a PLK under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of PLK Nucleic Acids and Polypeptides PLK nucleic acids and polypeptides are useful for identifying and testing agents that modulate PLK function and for other applications related to the involvement of PLK in the beta catenin pathway. PLK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a PLK protein for assays used to assess PLK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, N.J., 1996; Coligan J E et al, Current Protocols in Protein Science (eds.), 1999, John Wiley & Sons, New York). In particular embodiments, recombinant PLK is expressed in a cell line known to have defective beta catenin function. The recombinant cells are used in cell-based screening assay systems of the invention, as described further below.

The nucleotide sequence encoding a PLK polypeptide can be inserted into any appropriate expression vector. The necessary transcriptional and translational signals, including promoter/enhancer element, can derive from the native PLK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the PLK gene product, the expression vector can comprise a promoter operably linked to a PLK gene nucleic acid, one or more origins of replication, and, one or more selectable markers (e.g. thymidine kinase activity, resistance to antibiotics, etc.). Alternatively, recombinant expression vectors can be identified by assaying for the expression of the PLK gene product based on the physical or functional properties of the PLK protein in in vitro assay systems (e.g. immunoassays).

The PLK protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the PLK gene sequence is identified, the gene product can be isolated and purified using standard methods (e.g. ion exchange, affinity, and gel exclusion chromatography; centrifugation; differential solubility; electrophoresis). Alternatively, native PLK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of PLK or other genes associated with the beta catenin pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter PLK expression may be used in in vivo assays to test for activity of a candidate beta catenin modulating agent, or to further assess the role of PLK in a beta catenin pathway process such as apoptosis or cell proliferation. Preferably, the altered PLK expression results in a detectable phenotype, such as decreased or increased levels of cell proliferation, angiogenesis, or apoptosis compared to control animals having normal PLK expression. The genetically modified animal may additionally have altered beta catenin expression (e.g. beta catenin knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous PLK gene that results in a decrease of PLK function, preferably such that PLK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse PLK gene is used to construct a homologous recombination vector suitable for altering an endogenous PLK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270:8397-400).

In another embodiment, the transgenic animal is a "knock-in" animal having an alteration in its genome that results in altered expression (e.g., increased (including ectopic) or decreased expression) of the PLK gene, e.g., by introduction of additional copies of PLK, or by operatively inserting a regulatory sequence that provides for altered expression of an endogenous copy of the PLK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the beta catenin pathway, as animal models of disease and disorders implicating defective beta catenin function, and for in vivo testing of candidate therapeutic agents, such as those identified in screens described below. The candidate therapeutic agents are administered to a genetically modified animal having altered PLK function and phenotypic changes are compared with appropriate control animals such as genetically modified animals that receive placebo treatment, and/or animals with unaltered PLK expression that receive candidate therapeutic agent.

In addition to the above-described genetically modified animals having altered PLK function, animal models having defective beta catenin function (and otherwise normal PLK function), can be used in the methods of the present invention. For example, a beta catenin knockout mouse can be used to assess, in vivo, the activity of a candidate beta catenin modulating agent identified in one of the in vitro assays described below. Preferably, the candidate beta catenin modulating agent when administered to a model system with cells defective in beta catenin function, produces a detectable phenotypic change in the model system indicating that the beta catenin function is restored, i.e., the cells exhibit normal cell cycle progression.

Modulating Agents

The invention provides methods to identify agents that interact with and/or modulate the function of PLK and/or the beta catenin pathway. Modulating agents identified by the methods are also part of the invention. Such agents are useful in a variety of diagnostic and therapeutic applications associated with the beta catenin pathway, as well as in further analysis of the PLK protein and its contribution to the beta catenin pathway. Accordingly, the invention also provides methods for modulating the beta catenin pathway comprising the step of specifically modulating PLK activity by administering a PLK-interacting or -modulating agent.

As used herein, an "PLK-modulating agent" is any agent that modulates PLK function, for example, an agent that interacts with PLK to inhibit or enhance PLK activity or otherwise affect normal PLK function. PLK function can be affected at any level, including transcription, protein expression, protein localization, and cellular or extra-cellular activity. In a preferred embodiment, the PLK-modulating agent specifically modulates the function of the PLK. The phrases "specific modulating agent", "specifically modulates", etc., are used herein to refer to modulating agents that directly bind to the PLK polypeptide or nucleic acid, and preferably inhibit, enhance, or otherwise alter, the function of the PLK. These phrases also encompass modulating agents that alter the interaction of the PLK with a binding partner, substrate, or cofactor (e.g. by binding to a binding partner of a PLK, or to a protein/binding partner complex, and altering PLK function). In a further preferred embodiment, the PLK-modulating agent is a modulator of the beta catenin pathway (e.g. it restores and/or upregulates beta catenin function) and thus is also a beta catenin-modulating agent.

Preferred PLK-modulating agents include small molecule compounds; PLK-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the PLK protein or may be identified by screening compound libraries. Alternative appropriate modulators of this class are natural products, particularly secondary metabolites from organisms such as plants or fungi, which can also be identified by screening compound libraries for PLK-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the beta catenin pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific PLK-interacting proteins are useful in a variety of diagnostic and therapeutic applications related to the beta catenin pathway and related disorders, as well as in validation assays for other PLK-modulating agents. In a preferred embodiment, PLK-interacting proteins affect normal PLK function, including transcription, protein expression, protein localization, and cellular or extra-cellular activity. In another embodiment, PLK-interacting proteins are useful in detecting and providing information about the function of PLK proteins, as is relevant to beta catenin related disorders, such as cancer (e.g., for diagnostic means).

A PLK-interacting protein may be endogenous, i.e. one that naturally interacts genetically or biochemically with a PLK, such as a member of the PLK pathway that modulates PLK expression, localization, and/or activity. PLK-modulators include dominant negative forms of PLK-interacting proteins and of PLK proteins themselves. Yeast two-hybrid and variant screens offer preferred methods for identifying endogenous PLK-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

A PLK-interacting protein may be an exogenous protein, such as a PLK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). PLK antibodies are further discussed below.

In preferred embodiments, a PLK-interacting protein specifically binds a PLK protein. In alternative preferred embodiments, a PLK-modulating agent binds a PLK substrate, binding partner, or cofactor.

Antibodies

In another embodiment, the protein modulator is a PLK specific antibody agonist or antagonist. The antibodies have therapeutic and diagnostic utilities, and can be used in screening assays to identify PLK modulators. The antibodies can also be used in dissecting the portions of the PLK pathway responsible for various cellular responses and in the general processing and maturation of the PLK.

Antibodies that specifically bind PLK polypeptides can be generated using known methods. Preferably the antibody is specific to a mammalian ortholog of PLK polypeptide, and more preferably, to human PLK. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of PLK which are particularly antigenic can be selected, for example, by routine screening of PLK polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of a PLK. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of PLK or substantially purified fragments thereof. If PLK fragments are used, they preferably comprise at least 10, and more preferably, at least 20 contiguous amino acids of a PLK protein. In a particular embodiment, PLK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of PLK-specific antibodies is assayed by an appropriate assay such as a solid phase enzyme-linked immunosorbant assay (ELISA) using immobilized corresponding PLK polypeptides. Other assays, such as radioimmunoassays or fluorescent assays might also be used.

Chimeric antibodies specific to PLK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

PLK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg—to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Nucleic Acid Modulators

Other preferred PLK-modulating agents comprise nucleic acid molecules, such as antisense oligomers or double stranded RNA (dsRNA), which generally inhibit PLK activity. Preferred nucleic acid modulators interfere with the function of the PLK nucleic acid such as DNA replication, transcription, translocation of the PLK RNA to the site of protein translation, translation of protein from the PLK RNA, splicing of the PLK RNA to yield one or more mRNA species, or catalytic activity which may be engaged in or facilitated by the PLK RNA.

In one embodiment, the antisense oligomer is an oligonucleotide that is sufficiently complementary to a PLK mRNA to bind to and prevent translation, preferably by binding to the 5' untranslated region. PLK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev. 7:187-95; U.S. Pat. No. 5,235,033; and U.S. Pat. No. 5,378,841).

Alternative preferred PLK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a PLK-specific nucleic acid modulator is used in an assay to further elucidate the role of the PLK in the beta catenin pathway, and/or its relationship to other members of the pathway. In another aspect of the invention, a PLK-specific antisense oligomer is used as a therapeutic agent for treatment of beta catenin-related disease states.

Assay Systems

The invention provides assay systems and screening methods for identifying specific modulators of PLK activity. As used herein, an "assay system" encompasses all the components required for performing and analyzing results of an assay that detects and/or measures a particular event. In general, primary assays are used to identify or confirm a modulator's specific biochemical or molecular effect with respect to the PLK nucleic acid or protein. In general, secondary assays further assess the activity of a PLK modulating agent identified by a primary assay and may confirm that the modulating agent affects PLK in a manner relevant to the beta catenin pathway. In some cases, PLK modulators will be directly tested in a secondary assay.

In a preferred embodiment, the screening method comprises contacting a suitable assay system comprising a PLK polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates PLK activity, and hence the beta catenin pathway. The PLK polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of PLK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when PLK-interacting proteins are used in screens to identify small molecule modulators, the binding specificity of the interacting protein to the PLK protein may be assayed by various known methods such as substrate processing (e.g. ability of the candidate PLK-specific binding agents to function as negative effectors in PLK-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit PLK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a PLK polypeptide, a fusion protein thereof, or to cells or membranes bearing the polypeptide or fusion protein. The PLK polypeptide can be full length or a fragment thereof that retains functional PLK activity. The PLK polypeptide may be fused to another polypeptide, such as a peptide tag for detection or anchoring, or to another tag. The PLK polypeptide is preferably human PLK, or is an ortholog or derivative thereof as described above. In a preferred embodiment, the screening assay detects candidate agent-based modulation of PLK interaction with a binding target, such as an endogenous or exogenous protein or other substrate that has PLK-specific binding activity, and can be used to assess normal PLK gene function.

Suitable assay formats that may be adapted to screen for PLK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate PLK and beta catenin pathway modulators (e.g. U.S. Pat. No. 6,165,992 and U.S. Pat. No. 6,720,162 (kinase assays); U.S. Pat. Nos. 5,550,019 and 6,133,437 (apoptosis assays); and U.S. Pat. Nos. 5,976,782, 6,225,118 and 6,444, 434 (angiogenesis assays), among others). Specific preferred assays are described in more detail below.

Kinase Assays.

In some preferred embodiments the screening assay detects the ability of the test agent to modulate the kinase activity of a PLK polypeptide. In further embodiments, a cell-free kinase assay system is used to identify a candidate beta catenin modulating agent, and a secondary, cell-based assay, such as an apoptosis or hypoxic induction assay (described below), may be used to further characterize the candidate beta catenin modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-$^{33}$P ATP to a biotinylated peptide substrate; the substrate is captured on a streptavidin coated bead that transmits the signal (Beveridge M et al. J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Yet other assays for kinases involve uncoupled, pH sensitive assays that can be used for high-throughput screening of potential inhibitors or for determining substrate specificity. Since kinases catalyze the transfer of a gamma-phosphoryl group from ATP to an appropriate hydroxyl acceptor with the release of a proton, a pH sensitive assay is based on the detection of this proton using an appropriately matched buffer/indicator system (Chapman E and Wong C H (2002) Bioorg Med Chem. 10:551-5).

Apoptosis Assays.

Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:473041). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as Cellomics™ ArrayScan® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, and TOTO-3 fluorescent dye which labels DNA of dead cells with high cell membrane permeability.

An apoptosis assay system may comprise a cell that expresses a PLK, and that optionally has defective beta catenin function (e.g. beta catenin is over-expressed or under-expressed relative to wild-type cells). A test agent can be added to the apoptosis assay system and changes in induction of apoptosis relative to controls where no test agent is added, identify candidate beta catenin modulating agents. In some embodiments of the invention, an apoptosis assay may be used as a secondary assay to test a candidate beta catenin modulating agents that is initially identified using a cell-free assay system. An apoptosis assay may also be used to test whether PLK function plays a direct role in apoptosis. For example, an apoptosis assay may be performed on cells that over- or under-express PLK relative to wild type cells. Differences in apoptotic response compared to wild type cells suggests that the PLK plays a direct role in the apoptotic response. Apoptosis assays are described further in U.S. Pat. No. 6,133,437.

Cell Proliferation and Cell Cycle Assays.

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell Proliferation may also be examined using [3H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [3H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 960 AQueous Non-Radioactive Cell Proliferation Assay (Cat.#G5421).

Cell proliferation may also be assayed by colony formation in soft agar, or clonogenic survival assay (Sambrook et al., Molecular Cloning, Cold Spring Harbor (1989)). For example, cells transformed with PLK are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a PLK may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses a PLK, and that optionally has defective beta catenin function (e.g. beta catenin is over-expressed or under-expressed relative to wild-type cells). A test agent can be added to the assay system and changes in cell proliferation or cell cycle relative to controls where no test agent is added, identify candidate beta catenin modulating agents. In some embodiments of the invention, the cell proliferation or cell cycle assay may be used as a secondary assay to test a candidate beta catenin modulating agents that is initially identified using another assay system such as a cell-free assay system. A cell proliferation assay may also be used to test whether PLK function plays a direct role in cell proliferation or cell cycle. For example, a cell proliferation or cell cycle assay may be performed on cells that over- or under-express PLK relative to wild type cells. Differences in proliferation or cell cycle compared to wild type cells suggests that the PLK plays a direct role in cell proliferation or cell cycle.

Angiogenesis.

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a PLK, and that optionally has defective beta catenin function (e.g. beta catenin is over-expressed or under-expressed relative to wild-type cells). A test agent can be added to the angiogenesis assay system and changes in angiogenesis relative to controls where no test agent is added, identify candidate beta catenin modulating agents. In some embodiments of the invention, the angiogenesis assay may be used as a secondary assay to test a candidate beta catenin modulating agents that is initially identified using another assay system. An angiogenesis assay may also be used to test whether PLK function plays a direct role in cell proliferation. For example, an angiogenesis assay may be performed on cells that over- or under-express PLK relative to wild type cells. Differences in angiogenesis compared to wild type cells suggests that the PLK plays a direct role in angiogenesis. U.S. Pat. Nos. 5,976,782, 6,225,118 and 6,444,434, among others, describe various angiogenesis assays.

Hypoxic Induction.

The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with PLK in hypoxic conditions (such as with 0.1%

O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a PLK, and that optionally has defective beta catenin function (e.g. beta catenin is overexpressed or under-expressed relative to wild-type cells). A test agent can be added to the hypoxic induction assay system and changes in hypoxic response relative to controls where no test agent is added, identify candidate beta catenin modulating agents. In some embodiments of the invention, the hypoxic induction assay may be used as a secondary assay to test a candidate beta catenin modulating agents that is initially identified using another assay system. A hypoxic induction assay may also be used to test whether PLK function plays a direct role in the hypoxic response. For example, a hypoxic induction assay may be performed on cells that over- or under-express PLK relative to wild type cells. Differences in hypoxic response compared to wild type cells suggests that the PLK plays a direct role in hypoxic induction.

Cell Adhesion.

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Tubulogenesis.

Tubulogenesis assays monitor the ability of cultured cells, generally endothelial cells, to form tubular structures on a matrix substrate, which generally simulates the environment of the extracellular matrix. Exemplary substrates include Matrigel™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpha. Thus, in a further preferred embodiment, a tubulogenesis assay system comprises testing a PLK's response to a variety of factors, such as FGF, VEGF, phorbol myristate acetate (PMA), TNF-alpha, ephrin, etc.

Cell Migration.

An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing a PLK's response to a variety of pro-angiogenic factors, including tumor angiogenic and inflammatory angiogenic agents, and culturing the cells in serum free medium.

Sprouting Assay.

A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 μl of methocel-collagen solution and pipetted into individual wells of a 24 well plate to allow collagen gel polymerization. Test agents are added after 30 min by pipetting 100 μl of 10-fold concentrated working dilution of the test substances on top of the gel. Plates are incubated at 37° C.

for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the PLK protein. Methods for testing antibody affinity and specificity are well known in the art (Harlow and Lane, 1988, 1999, supra). The enzyme-linked immunosorbant assay (ELISA) is a preferred method for detecting PLK-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance PLK gene expression, preferably mRNA expression. In general, expression analysis comprises comparing PLK expression in like populations of cells (e.g., two pools of cells that endogenously or recombinantly express PLK) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that PLK mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the PLK protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve PLK mRNA expression, may also be used to test nucleic acid modulators.

Secondary Assays

Secondary assays may be used to further assess the activity of PLK-modulating agent identified by any of the above methods to confirm that the modulating agent affects PLK in a manner relevant to the beta catenin pathway. As used herein, PLK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with PLK.

Secondary assays generally compare like populations of cells or animals (e.g., two pools of cells or animals that endogenously or recombinantly express PLK) in the presence and absence of the candidate modulator. In general, such assays test whether treatment of cells or animals with a candidate PLK-modulating agent results in changes in the beta catenin pathway in comparison to untreated (or mock- or placebo-treated) cells or animals. Certain assays use "sensitized genetic backgrounds", which, as used herein, describe cells or animals engineered for altered expression of genes in the beta catenin or interacting pathways.

Cell-Based Assays

Cell based assays may detect endogenous beta catenin pathway activity or may rely on recombinant expression of beta catenin pathway components. Any of the aforementioned assays may be used in this cell-based format. Candidate modulators are typically added to the cell media but may also be injected into cells or delivered by any other efficacious means.

Animal Assays

A variety of non-human animal models of normal or defective beta catenin pathway may be used to test candidate PLK modulators. Models for defective beta catenin pathway typically use genetically modified animals that have been engineered to mis-express (e.g., over-express or lack expression in) genes involved in the beta catenin pathway. Assays generally require systemic delivery of the candidate modulators, such as by oral administration, injection, etc.

In a preferred embodiment, beta catenin pathway activity is assessed by monitoring neovascularization and angiogenesis. Animal models with defective and normal beta catenin are used to test the candidate modulator's affect on PLK in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the PLK. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on PLK is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the PLK endogenously are injected in the flank, $1\times10^5$ to $1\times10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific PLK-modulating agents are useful in a variety of diagnostic and therapeutic applications where disease or disease prognosis is related to defects in the beta catenin pathway, such as angiogenic, apoptotic, or cell proliferation disorders. Accordingly, the invention also provides methods for modulating the beta catenin pathway in a cell, preferably a cell pre-determined to have defective or impaired beta catenin function (e.g. due to overexpression, underexpression, or misexpression of beta catenin, or due to gene mutations), comprising the step of administering an agent to the cell that specifically modulates PLK activity. Preferably, the modulating agent produces a detectable phenotypic change in the cell indicating that the beta catenin function is restored. The phrase "function is restored", and equivalents, as used herein, means that the desired phenotype is achieved, or is brought closer to normal compared to untreated cells. For example, with restored beta catenin function, cell proliferation and/or progression through cell cycle may normalize, or be brought closer to normal relative to untreated cells. The invention also provides methods for treating disorders or disease associated with impaired beta catenin function by administering a therapeutically effective amount of a PLK-modulating agent that modulates the beta catenin pathway. The invention further provides methods for modulating PLK function in a cell, preferably a cell pre-determined to have defective or impaired PLK function, by administering a PLK-modulating agent. Additionally, the invention provides a method for treating disorders or disease associated with impaired PLK function by administering a therapeutically effective amount of a PLK-modulating agent.

The discovery that PLK is implicated in beta catenin pathway provides for a variety of methods that can be employed for the diagnostic and prognostic evaluation of diseases and disorders involving defects in the beta catenin pathway and for the identification of subjects having a predisposition to such diseases and disorders.

Various expression analysis methods can be used to diagnose whether PLK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective beta catenin signaling that express a PLK, are identified as amenable to treatment with a PLK modulating agent. In a preferred application, the beta catenin defective tissue overexpresses a PLK relative to normal tissue. For example, a Northern blot analysis of mRNA from tumor and normal cell lines, or from tumor and matching normal tissue samples from the same patient, using full or partial PLK cDNA sequences as probes, can determine whether particular tumors express or overexpress PLK. Alternatively, the TaqMan® is used for quantitative RT-PCR analysis of PLK expression in cell lines, normal tissues and tumor samples (PE Applied Biosystems).

Various other diagnostic methods may be performed, for example, utilizing reagents such as the PLK oligonucleotides, and antibodies directed against a PLK, as described above for: (1) the detection of the presence of PLK gene mutations, or the detection of either over- or under-expression of PLK mRNA relative to the non-disorder state; (2) the detection of either an over- or an under-abundance of PLK gene product relative to the non-disorder state: and (3) the detection of perturbations or abnormalities in the signal transduction pathway mediated by PLK.

Kits for detecting expression of PLK in various samples, comprising at least one antibody specific to PLK, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in PLK expression, the method comprising: a) obtaining a biological sample from the patient; b) contacting the sample with a probe for PLK expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* Beta Catenin Screen

Two dominant loss of function screens were carried out in *Drosophila* to identify genes that interact with the Wg cell signaling molecule, beta-catenin (Riggleman et al. (1990) Cell 63:549-560; Peifer et al. (1991) Development 111:1029-1043). Late stage activation of the pathway in the developing *Drosophila* eye leads to apoptosis (Freeman and Bienz (2001) EMBO reports 2: 157-162), whereas early stage activation leads to an overgrowth phenotype. We discovered that ectopic expression of the activated protein in the wing results in changes of cell fate into ectopic bristles and wing veins.

Each transgene was carried in a separate fly stock:
Stocks and genotypes were as follows:
eye overgrowth transgene: isow; P{3.5 eyeless-Gal4}; P{arm(S56F)-pExp-UAS)}/TM6b;
eye apoptosis transgene: y w; P{arm(S56F)-pExp-GMR}/CyO; and
wing transgene: P{arm(ΔN)-pExp-VgMQ}/FM7c In the first dominant loss of function screen, females of each of these three transgenes were crossed to a collection of males containing genomic deficiencies. Resulting progeny containing the transgene and the deficiency were then scored for the effect of the deficiency on the eye apoptosis, eye overgrowth, and wing phenotypes, i.e., whether the deficiency enhanced, suppressed, or had no effect on their respective phenotypes. All data was recorded and all modifiers were retested with a repeat of the original cross. Modifying deficiencies of the phenotypes were then prioritized according to how they modified each of the three phenotypes.

Transposons contained within the prioritized deficiencies were then screened as described. Females of each of the three transgenes were crossed to a collection of 4 types of transposons (3 piggyBac-based and 1 P-element-based). The resulting progeny containing the transgene and the transposon were scored for the effect of the transposon on their respective phenotypes. All data was recorded and all modifiers were retested with a repeat of the original cross. Modifiers of the phenotypes were identified as either members of the Wg pathway, components of apoptotic related pathways, components of cell cycle related pathways, or cell adhesion related proteins.

In the second dominant loss of function screen, females of the eye overgrowth transgene were crossed to males from a collection of 3 types of piggyBac-based transposons. The resulting progeny containing the transgene and the transposon were scored for the effect of the transposon on the eye overgrowth phenotype. All data was recorded and all modifiers were retested with a repeat of the original cross. Modifiers of the phenotypes were identified as either members of the Wg pathway, components of cell cycle related pathways, or cell adhesion related proteins.

*Drosophila* POLO was identified as a suppressor from the screen. Orthologs of the modifiers are referred to herein as PLK.

BLAST analysis (Altschul et al., supra) was employed to identify orthologs of *Drosophila* modifiers. For example, representative sequence from PLK, GI#21361433 (SEQ ID NO:6), shares 56% amino acid identity with the *Drosophila* POLO.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the Caenorhabditis elegans genome and identification of human orthologs. Genome Res. 2000 November; 10(11): 1679-89) programs. For example, the Protein kinase domain (PFAM 00069) of PLK from GI#21361433 (SEQ ID NO:6) is located at approximately amino acid residues 12-265.

II. High-Throughput In Vitro Fluorescence Polarization Assay

Fluorescently-labeled PLK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of PLK activity.

III. High-Throughput In Vitro Binding Assay.

$^{33}$P-labeled PLK peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells' of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate beta catenin modulating agents.

IV. Immunoprecipitations and Immunoblotting

For coprecipitation of transfected proteins, 3×10$^6$ appropriate recombinant cells containing the PLK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified PLK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation (Mg2$^+$ or Mn$^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TaqMan® analysis was used to assess expression levels of the disclosed genes in various samples.

RNA was extracted from each tissue sample using Qiagen (Valencia, Calif.) RNeasy kits, following manufacturer's protocols, to a final concentration of 50 ng/μl. Single stranded cDNA was then synthesized by reverse transcribing the RNA samples using random hexamers and 500 ng of total RNA per reaction, following protocol 430-4965 of Applied Biosystems (Foster City, Calif.).

Primers for expression analysis using TaqMan® assay (Applied Biosystems, Foster City, Calif.) were prepared according to the TaqMan® protocols, and the following criteria: a) primer pairs were designed to span introns to eliminate genomic contamination, and b) each primer pair produced only one product. Expression analysis was performed using a 7900HT instrument.

TaqMan® reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV (all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| Seg ID No | 1 |
|---|---|
| Breast | 61% |
| # of Pairs | 36 |
| Colon | 38% |
| # of Pairs | 40 |
| Head And Neck | 54% |
| # of Pairs | 13 |
| Kidney | 52% |
| # of Pairs | 21 |
| Liver | 78% |
| # of Pairs | 9 |
| Lung | 68% |
| # of Pairs | 40 |
| Lymphoma | 75% |
| # of Pairs | 4 |
| Ovary | 68% |
| # of Pairs | 19 |
| Pancreas | 75% |
| # of Pairs | 12 |
| Placenta | ND |
| # of Pairs | ND |
| Prostate | 12% |
| # of Pairs | 24 |
| Skin | 57% |
| # of Pairs | 7 |
| Stomach | 82% |
| # of Pairs | 11 |
| Testis | 25% |
| # of Pairs | 8 |
| Thyroid Gland | 21% |
| # of Pairs | 14 |
| Uterus | 61% |
| # of Pairs | 23 |

VII. PLK Functional Assays

RNAi experiments were carried out to knock down expression of PLK (SEQ ID NO:1) in various cell lines using small interfering RNAs (siRNA, Elbashir et al, supra).

Effect of PLK RNAi on cell proliferation and growth. [$^3$H]-thymidine incorporation assay, as described above, was employed to study the effects of decreased PLK expression on cell proliferation. The results of these experiments indicated that RNAi of PLK decreases proliferation in LOVO and HT29 colon cancer cells and PC3 prostate cancer cells. Standard colony growth assays, as described above, were employed to study the effects of decreased PLK expression on cell growth. Results indicated that RNAi of PLK decreased proliferation in HT29 and SW480 colon cancer cells.

Effect of PLK RNAi on apoptosis. Multi-parameter apoptosis assays, as described above, was employed to study the effects of decreased PLK expression on apoptosis. Results indicated that RNAi of SEQ ID NO:1 increased TOTO uptake (indicating high cell membrane permeability), caspase activity (indicating intermediate stage apoptosis), and nuclear swelling (indicating increased early stage apoptosis) in A549 lung cancer cells. Further, RNAi of SEQ ID NO: 1 increased PARP cleavage (indicating late stage apoptosis) in PC3 prostate cancer cells.

TOPFLASH beta-catenin reporter assay. Factors of the TCF/LEF HMG domain family (TCFs) exist in vertebrates, *Drosophila melanogaster* and Caenorhabditis elegans. Upon Wingless/Wnt signaling, Armadillo/beta-catenin associate with nuclear TCFs and contribute a trans-activation domain to the resulting bipartite transcription factor. So, transcriptional activation of TCF target genes by beta-catenin appears to be a central event in development and cellular transformation. Topflash beta-catenin luciferase gene reporter assay is used as a tool to measures activity of various genes in the beta-catenin pathway by transcriptional activation of TCFs (Korinek, V, et al. (1998) Molecular and Cellular Biology 18: 1248-1256). Briefly, cells are co-transfected with TOPFLASH plasmids containing TCF binding sites driving luciferase, and gene of interest. Transfected cells are then analyzed for luciferase activity. RNAi of SEQ ID NO: 1 caused decreased luciferase activity as compared with normal controls in LX1 lung cancer cells and in SW480 and LOVO colon cancer cells. Alternatively, overexpression of SEQ ID NO: 1 caused increased luciferase activity in PC3 prostate cancer cells.

Transcriptional reporter assays. Effects of overexpressed PLK on expression of various transcription factors was also studied. Overexpressed PLK (SEQ ID NO: 1) caused an increased expression of AP1 (activator protein 1) transcription factor. Additionally, other transcriptional reporter assay was also performed to measure the effects of overexpressed PLK on expression of various transcription factors. In this assay, rat intestinal epithelial cells (RIEs) or NIH3T3 cells were co-transfected with reporter constructs containing various transcription factors and luciferase along with PLK. Luciferase intensity was then measured as the readout for transcriptional activation due to overexpression of the PLK. Overexpressed PLK of SEQ ID NO: 1 caused an increased expression of AP1 (activator protein 1) transcription factor.

Taken together, these functional experiments indicate a relationship between PLK and beta catenin pathway.

What is claimed is:

1. A method of identifying a candidate beta catenin pathway modulating agent, said method comprising the steps of:
    (a) providing an assay system comprising a Polo Like Kinase 4 (PLK4) polypeptide or nucleic acid, wherein the assay system comprises cultured cells that express the PLK4 polypeptide and have defective beta-catenin function and wherein the assay system is capable of detecting the activity or expression of PLK4;
    (b) contacting the assay system with a test agent; and
    (c) determining the activity or expression of the PLK4 polypeptide or nucleic acid in the assay system in the presence or absence of the test agent of step (b), wherein a change in PLK4 activity or expression between the presence and absence of the test agent identifies the test agent as a candidate beta catenin pathway modulating agent.

2. The method of claim 1 wherein the assay system includes a screening assay comprising a PLK polypeptide, and the candidate test agent is a small molecule modulator.

3. The method of claim 2 wherein the assay is a kinase assay.

4. The method of claim 1 wherein the assay system is selected from the group consisting of an apoptosis assay system, a cell proliferation assay system, an angiogenesis assay system, and a hypoxic induction assay system.

5. The method of claim 1 wherein the assay system includes a binding assay comprising a PLK polypeptide and the candidate test agent is an antibody.

6. The method of claim 1 wherein the assay system includes an expression assay comprising a PLK4 nucleic acid and the candidate test agent is a nucleic acid modulator.

7. The method of claim 6 wherein the nucleic acid modulator is an antisense oligomer.

8. The method of claim 6 wherein the nucleic acid modulator is a phosphothioate morpholino oligomer (PMO).

9. The method of claim 1 additionally comprising:
    (d) administering the candidate beta catenin pathway modulating agent identified in (c) to a model system comprising cells defective in beta catenin function and, detecting a phenotypic change in the model system that indicates that the beta catenin function is restored.

10. The method of claim 9 wherein the model system is a mouse model with defective beta catenin function.

11. A method of identifying a candidate beta catenin pathway modulating agent, said method comprising the steps of:
    (a) providing a first assay system comprising a Polo Like Kinase 4 (PLK4) polypeptide or nucleic acid, wherein the assay system comprises cultured cells that express the PLK4 polypeptide and wherein the assay system is capable of detecting the activity or expression of PLK4;
    (b) contacting the assay system with a test agent;
    (c) determining the activity or expression of the PLK4 polypeptide or nucleic acid in the assay system in the presence or absence of the test agent of step (b), wherein a change in PLK4 activity or expression between the presence and absence of the test agent identifies the test agent as a candidate beta catenin pathway modulating agent;
    (d) providing a second assay system comprising cultured cells expressing PLK4 capable of detecting a change in the beta catenin pathway,
    (e) contacting the second assay system with the test agent of step (b); and
    (f) measuring the beta catenin pathway in the presence or absence of the test agent, wherein the beta catenin pathway is measured by measuring the transcriptional activation of transcription factor (TCF) target genes or by measuring the transcriptional activation of beta catenin and wherein the detection of a difference in the presence and absence of the test agent confirms the test agent as a candidate beta catenin pathway modulating agent.

12. The method of claim 11 wherein the first assay system and/or the second assay system comprises cultured cells having defective beta catenin function.

13. The method of claim 11 wherein the secondary assay system comprises a nonhuman animal.

14. The method of claim 13 wherein the non-human animal mis-expresses a beta catenin pathway gene.

* * * * *